(12) United States Patent
Jordan

(10) Patent No.: US 8,480,681 B2
(45) Date of Patent: Jul. 9, 2013

(54) PRESSURED SYRINGE FOR THE INJECTION OF A VISCOUS LIQUID THROUGH A CANNULATED SURGICAL SCREW BONE FILLER ADAPTER

(76) Inventor: Christopher Jordan, Midwest City, OK (US)

(*) Notice: Subject to any disclaimer, the term of this patent is extended or adjusted under 35 U.S.C. 154(b) by 311 days.

(21) Appl. No.: 12/803,816

(22) Filed: Jul. 7, 2010

(65) Prior Publication Data

US 2010/0298836 A1 Nov. 25, 2010

Related U.S. Application Data

(63) Continuation-in-part of application No. 12/454,696, filed on May 21, 2009, now Pat. No. 8,231,632.

(51) Int. Cl.
*A61B 17/58* (2006.01)
(52) U.S. Cl.
USPC ............................................. 606/94; 606/304
(58) Field of Classification Search
USPC ...................................... 606/92–94
See application file for complete search history.

(56) References Cited

U.S. PATENT DOCUMENTS

| | | | |
|---|---|---|---|
| 2,283,915 A | 5/1942 | Cole | |
| 3,353,718 A | 11/1967 | McLay | |
| 3,750,667 A | 8/1973 | Pshenichny | |
| 4,277,184 A | 7/1981 | Solomon | |
| 5,078,690 A | 1/1992 | Ryan | |
| 5,540,657 A | 7/1996 | Kurjan | |
| 5,591,188 A | 1/1997 | Waisman | |
| 6,053,899 A | 4/2000 | Slanda | |
| 6,997,904 B2 | 2/2006 | Sculati | |
| 7,041,084 B2 | 5/2006 | Fojtik | |
| 7,604,618 B2 | 10/2009 | Dixon | |
| 2004/0030345 A1 | 2/2004 | Aurin | |
| 2007/0185496 A1 | 8/2007 | Beckman | |
| 2009/0281549 A1* | 11/2009 | Dixon | 606/94 |
| 2009/0292290 A1* | 11/2009 | Truckai et al. | 606/94 |
| 2010/0004656 A1* | 1/2010 | Marins Dos Reis, Jr. | 606/93 |
| 2010/0094307 A1* | 4/2010 | Evans et al. | 606/94 |

* cited by examiner

*Primary Examiner* — Kevin T Truong
*Assistant Examiner* — Michael Araj

(57) ABSTRACT

A pressurized syringe used to inject a viscous liquid through an adapter attached to a bone filler adapter into a cannulated surgical screw utilizing the cannulated surgical screw as a port to inject bone void filler into a bone void within a bone cavity during the course of a surgical repair to attach, repair and secure broken or separated bone fragments and providing a more secure bone anchor matrix within which the surgical screw is set.

2 Claims, 9 Drawing Sheets

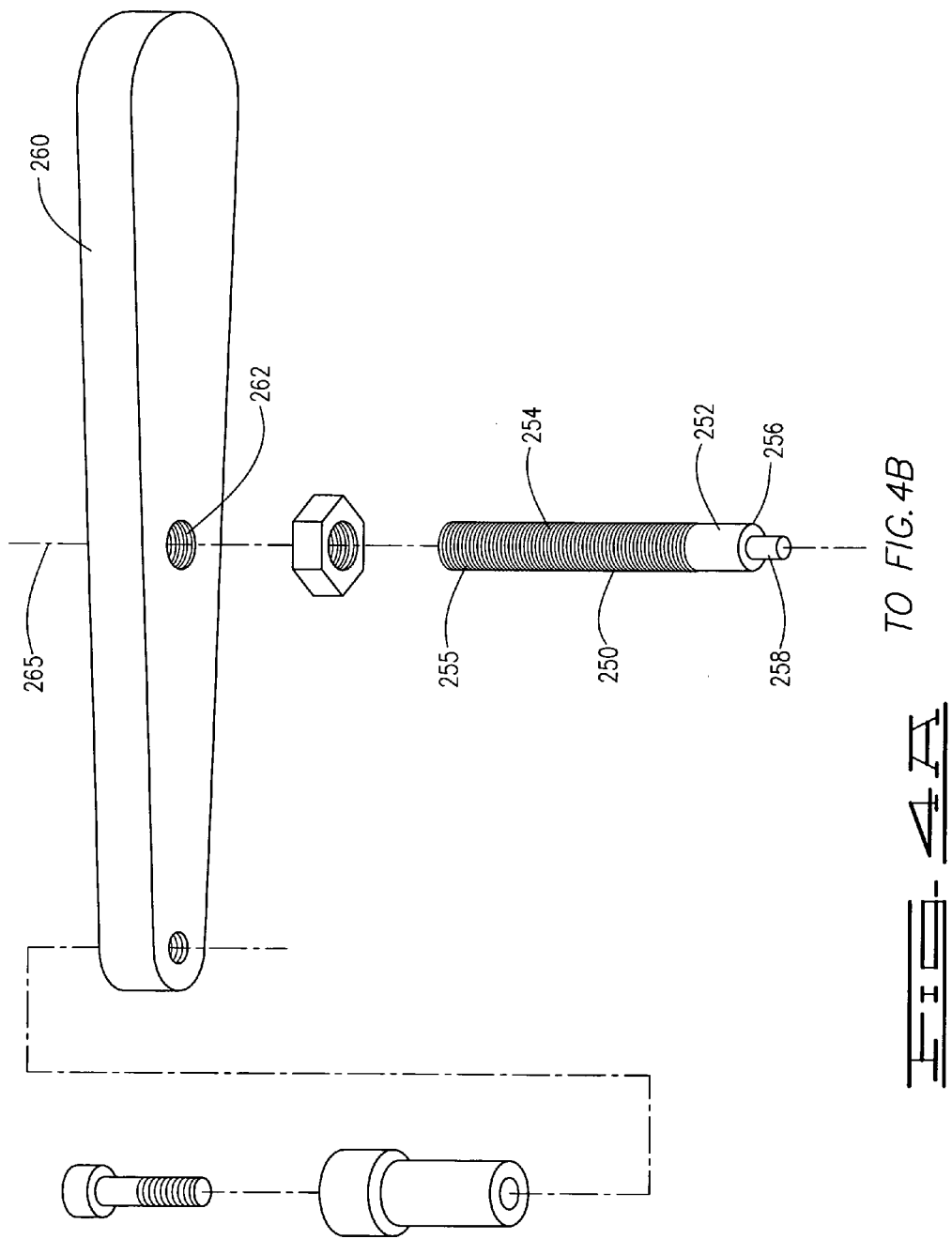

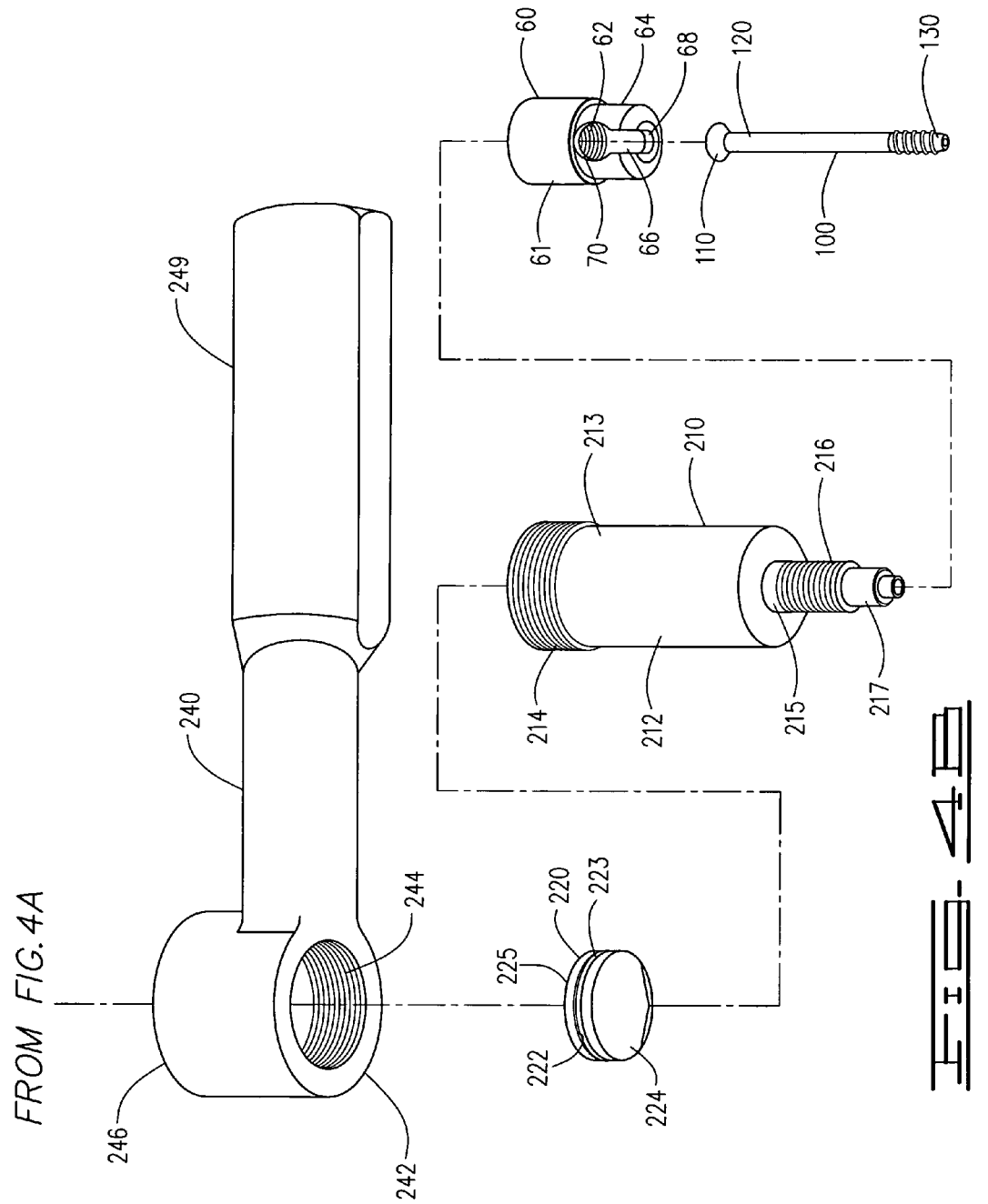

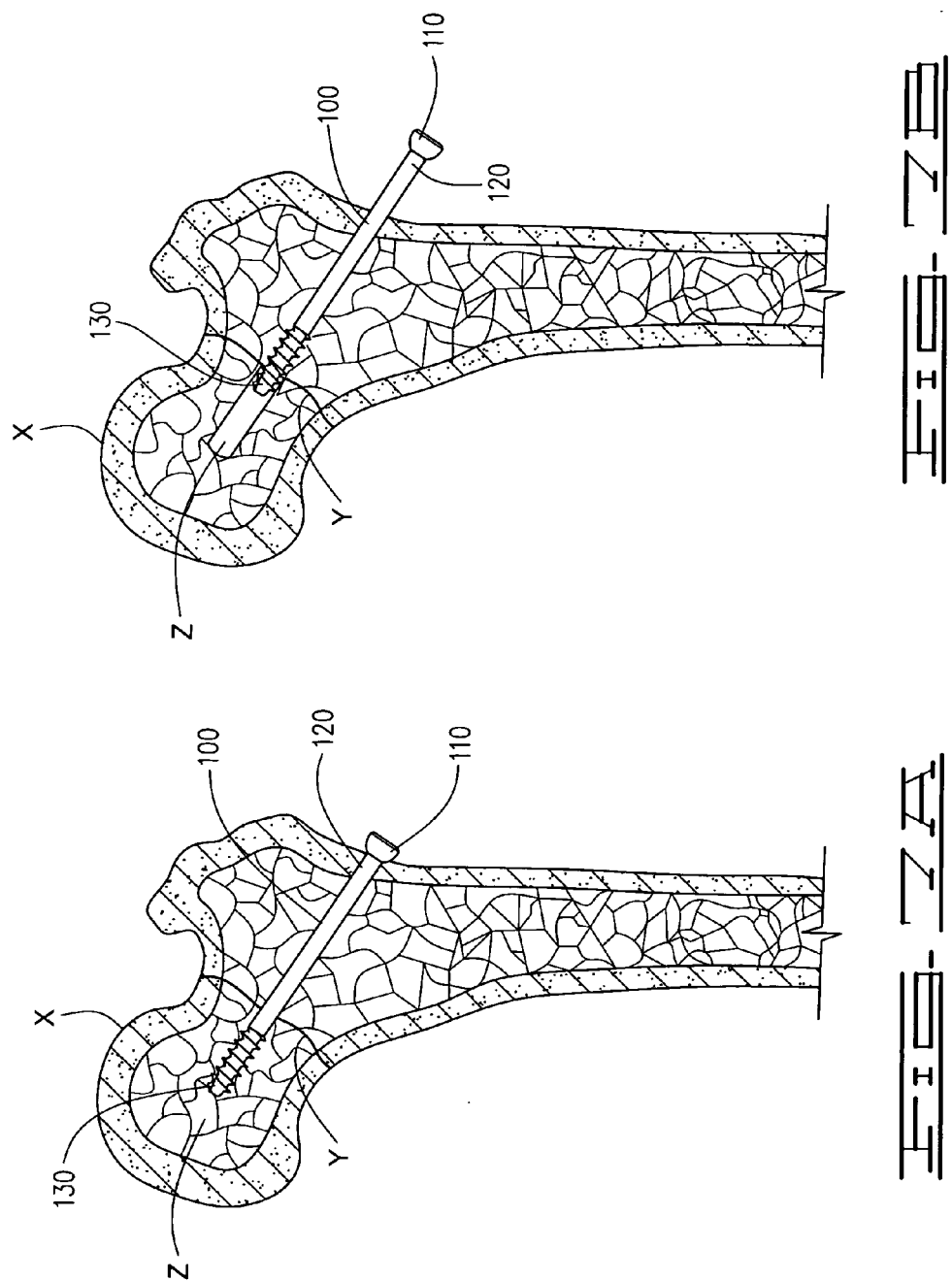

PRESSURED SYRINGE FOR THE INJECTION OF A VISCOUS LIQUID THROUGH A CANNULATED SURGICAL SCREW BONE FILLER ADAPTER

CROSS REFERENCE TO RELATED APPLICATIONS

This is a Continuation-in-Part Application of U.S. patent application Ser. No. 12/454,696, filed by the same inventors on May 21, 2009, now U.S. Pat. No. 8,231,632 with reference made to pending U.S. patent application Ser. No. 12/456,577 filed on Jun. 18, 2009 by at least one common inventor, Christopher Jordan.

BACKGROUND OF THE INVENTION

1. Field of Invention

A pressurized syringe used to inject a viscous liquid through an adapter attached to a bone filler adapter into a cannulated surgical screw utilizing the cannulated surgical screw as a port to inject bone void filler into a bone void within a bone cavity during the course of a surgical repair to attach, repair and secure broken or separated bone fragments and providing a more secure bone anchor matrix within which the surgical screw is set.

2. Description of Prior Art

A preliminary review of prior art patents was conducted by the applicant which reveal no prior art patents in a similar field or having similar use in the field of orthopedic surgery. The disclosed prior art inventions do not disclose the same or similar elements as the present pressurized syringe attaching to a cannulated screw bone filler adapter, nor do they present the material components in a manner contemplated or anticipated in the prior art.

Bone cements are known in the art of orthopedic surgery and have been discussed in articles including *The use of Calcium Phosphate Bone Cement in fracture Treatment*, Bajammal, Sohail S., et al., Journal of Bone and Joint Surgery, Volume 90, pgs. 1186-1196, and articles referenced therein and in U.S. Patent Application No. 2007/0032567 to Beyar. Methods of injection of a bone filler are disclosed in U.S. Patent Application No. 2009/0054934, to Beyar, which provide methods for accessing a void in the bone, introduction of bone cement into a void, introduction of an expandable filler into the void, expanding the filler and allowing the cement to set. This application clearly points out a danger in contamination of non-intentional tissue surrounding the fracture site with the bone cement by leakage or by overfill causing further damage to the affected bone being repaired and also by introduction of the bone cement through mistake or accident. Other methods employing the use of a surgical procedure known as Kyphoplasty, wherein a balloon is inflated within a bone void with the balloon further filled with a bone filler material to minimize collateral exposure to the bone cement, is demonstrated in U.S. Patent Application No. 2006/0122625 to Truckai.

Another patent application, U.S. patent Application No 2007/0055257 to Vaccaro, has attempted to utilize modified cannulated screws to accomplish an injection of a syringe containing a bone filler, the head of the cannulated screw having an externally threaded inner head adapted to a syringe having an internally threaded collar with an injector tip which enters the longitudinal central bore in the cannulated screw, the cannulated screw having a side discharge port to release the bone filler injected into the central bore.

The present adapter and pressurized syringe utilizes a typical prior art cannulated surgical screw as shown in FIGS. 1A-1C, available from surgical supply companies including MIKROMED, DEPUY®, OSTEOMED® and SYNTHES®. The adapted secures to the head of the cannulated screw by screwing the two threaded components together, locking the adapter to the head of the cannulated screw. A pressurized syringe containing a viscous liquid, in the present case a bone cement, attaches to the adapter, dispenses the viscous liquid through an outer threaded end into an internally threaded head cap of the upper component of the adapter, after which the viscous liquid or bone cement contained within pressurized syringe is injected through the adapter and the longitudinal central bore of the cannulated screw through the tip of the cannulated screw into a bone void below the tip of the cannulated screw which will secure the tip of the cannulated screw into the bone void filler cement subsequent to the hardening of the cement. Anchoring the tip of the surgical screw would reduce the chance of the screw backing out of the bone, which is not an uncommon occurrence, in the same manner that filling a post hole with cement to anchor a fencepost stabilizes and supports the fencepost over simply ramming the fencepost into the dirt.

Several syringes are disclosed in the prior art which appear to apply a greater force than a common syringe employing a plunger and a cylinder. Prior art devices include a bone cement syringe which provides a syringe within a syringe, the inner syringe filled with paste, and the outer syringe holding the inner syringe with the outer syringe having a threaded plunger system, as indicated in U.S. Patent Application Publication 2004/0030345 to Aurin. A bone cement mixer and dispensing syringe is also disclosed in U.S. Pat. No. 4,277,184 to Solomon. A syringe device for injecting bone cement into a cannula, or hollow tube inserted into a bone, is disclosed in U.S. Patent Publication No. 2007/0185496 to Beckman.

Syringes having a threaded plunger in relation to the syringe body include U.S. Pat. No. 2,283,915 to Cole and U.S. Pat. No. 3,353,718 to McLay. Portions of syringes provide prior art references including U.S. Pat. No. 7,604,618 to Dixon, disclosing a high pressure injection syringe having an expanded and reinforced plunger tip having an O-ring sealer used with a screw engaged plunger with a great emphasis involved in the disclosure of the viscoselective seal involved in the tip of the plunger. Another viscous fluid syringe, disclosed in U.S. Pat. No. 6,997,904 to Sculati, provides a locking head assembly for retaining the syringe in the cylindrical syringe sleeve which includes a top plate and a locking flange which engages with the flange for locking the head assembly to the cylinder. The plunger in the syringe is discarded and when the locking head assembly is placed on the cylindrical syringe sleeve an internal flange with a gasket located on it is inserted into the top of the syringe chamber forming a seal. Other high pressure syringes are indicated in U.S. Pat. Nos. 7,041,084 to Fojtik, 5,540,657 to Kurjan and 5,078,690 to Ryan.

However, none of the prior art devices, together or individually, disclose the pressurized syringe which is used in conjunction with the bone filler adapter and a cannulated screw forming a complete and secure seal for the injection of a bone cement or other viscous liquid.

SUMMARY OF THE INVENTION

A most common fracture of a bone occurs when the head of the bone, most commonly a femur, humerus, radius, or tibia, is broken from the remainder of the bone. This repair is a difficult repair and ordinarily requires a surgical intervention. A most common repair involves the insertion of one or more screws to attach the broken end of the bone to the remainder of the bone through use of surgical screws. These screws are placed in the bone either to hold bone to bone or to hold the bone together by use of a bracket or brace attached to the fixed portion of the bone and also attaching the broken portion of the bone, most commonly the head, to the bracket to allow the aligned bones to grow together again.

Take for example a situation where the neck of the femur is fractured. This is not uncommon, especially in the elderly or those involved in traumatic associated injuries. The fracture occurs along the neck and thus the head of the femur must be joined to the upper end of the femur through the trochanter. Once aligned, a pathway is drilled from the lateral side of the femur below the greater trochanter, through the neck of the femur and into the inner cavity of the head of the femur. Inside the head of the femur is a space which is filled with a very porous bone material, but much less dense than the bone itself. As a person get older, this inner portion of the head becomes more porous and eventually creates a large void or extremely porous space within the head. This poses a fixation problem for the placement and secure anchoring of a surgical screw inserted within the drilled pathway. Thus, several screws must be used to make a secure attachment of the head to the femur unless something could be done to file the bone void or very porous space with some material strong enough to provide an anchoring matrix to further secure the tip of the surgical screw into the bone to prevent it from becoming loose or being backed out over time.

It is known in the art that use of bone cement is a material with a history of success in bone to bone connection, delivered in a paste or liquid and hardening into a solid biocompatible material. Surgical success has been demonstrated by statistical comparison. Companies provide this bone cement in solid materials which are reduced to a paste or liquid prior to use, or deliver bone cements in pre-filled syringes. Prior art has demonstrated use of bone cements applied externally to the surface of a bone, or injected into space around or below a vertebrae in a process known as Kyphoplasty to repair fractured vertebrae by elevating the vertebrae to a normal position and then injecting a balloon used to lift the vertebrae with the bone cement to hold and retain the vertebrae in the elevated position caused by the balloon. Injection of the bone cement is through a tube inserted through the back and into the inflated balloon during the surgical procedure, which last about an hour for each vertebrae, takes about a day to recover and instantly provides a permanent relief from pain caused by vertebral compression. However, this process has not been used in the past for repair or reduction of the reattachment of the end of a bone using surgical screws. There is some discussion of a modified cannulated screw used in repair of a vertebrae to provide access through the cannulated screw during surgery by providing a side access through the screw for a spinal rod or other surgical tool after placement of the screw.

Currently there is no technique or procedure disclosing the use of a cannulated screw as a delivery means for the injection of a liquid or gel into a bone void as disclosed in the present syringe and bone filler adapter secured to a conventional cannulated bone screw. There is no disclosed procedure for filling a bone void through injection as disclosed in the present device using the disclosed pressurized syringe. There is no mention in any prior art of an adapter which is located between a syringe and a cannulated surgical screw to prevent spillage or contamination of surrounding tissue with bone cement which seals a delivery passage between the end of a syringe and the head of a cannulated surgical screw. There is also no disclosed method or apparatus to inject a bone void with bone cement to secure a surgical screw within the bone. Thus, the disclosed adapter is in no way mentioned in prior art, the procedure for the use of the disclosed adapter is not revealed in prior art and thus not anticipated nor contemplated in any prior art. No method or device is disclosed in any prior art to address the issue of providing a more secure anchor within a bone void for a surgical screw, cannulated or other, so it is unlikely that any prior art patent would be designed or adapted to a similar use to resolve a similar issue.

Filling a bone void to provide a more stable anchoring matrix would provide a more secure anchoring of a surgical screw, requiring fewer screws and providing a better fixation of the bone repair. As a screw is already being used for this procedure, providing the screw as an already available cannulated surgical screw would require no additional surgical procedure than already being done. The cannulated screw, having already been inserted into a drilled location through the bone, is already located with the tip of the surgical screw in the area where the bone void is presented, already places the tip of the surgical screw in an ideal location which has already been interrupted for the placement of a bone filler cement within the bone void of the bone being repaired. The syringe and adapter are employing the already used cannulated surgical screw as a port for the injection of bone cement through the longitudinal channel directed to the tip of the surgical screw, after having fully inserted the surgical screw into the bone and then partially backed it out for the injection of the bone void cement into the bone void through the cannulated surgical screw, and then reinserting the surgical screw to its full insertion.

The disclosed syringe attaching to the adapter and providing a secure connection between a cannulated surgical screw and the syringe filled with a quite viscous bone filler cement to deliver the bone filler cement into a bone void for a secure attachment of a fully inserted surgical screw into a bone. The disclosed syringe is securely attached to the adapter which is installed upon the head of the cannulated surgical screw during application of a force required to expel the bone cement from the syringe to the opposing end of the adapter. The disclosed adapter can be used with existing and available surgical appliances and during an existing and currently used surgical procedure to inject bone filler cement into a directed bone without contamination of the surgical tissue with the bone filler cement.

DESCRIPTION OF THE DRAWINGS

The following drawings are submitted with this utility patent application.

FIG. 4A is an exploded view of a rotating syringe crank handle.

FIG. 4B is an expanded view of the syringe body grip member and upper syringe retainer, the syringe body and plunger and the cannulated screw and bone filler adapter.

FIG. 6B is a side cross sectional view of the pressurized syringe assembly attached to the cannulated screw bone filler adapter and a cannulated surgical screw with the upper syringe body and the lower member fully secured forming a secure seal and inserting the cylindrical tip of the upper member within the upper portion of the longitudinal bore of the cannulated surgical screw, for the injection of the bone filler cement, or other viscous liquid, through the longitudinal bore and eventually out of the lower end of the longitudinal bore.

FIG. 7A is a cross sectional view of the fractured head of a femur indicating a full insertion of a cannulated surgical screw to secure the fracture site.

FIG. 7B is a cross sectional view of the fractured head of a femur indicating a backout position of the cannulated surgical screw as shown in FIG. 6A, positioning the cannulated surgical screw in the proper position for application of the cannulated screw bone filler adapter and the bone filler dispenser for insertion of bone filler cement into the bone void within the fractured head of the femur.

DESCRIPTION OF THE PREFERRED EMBODIMENT

Figure 1:
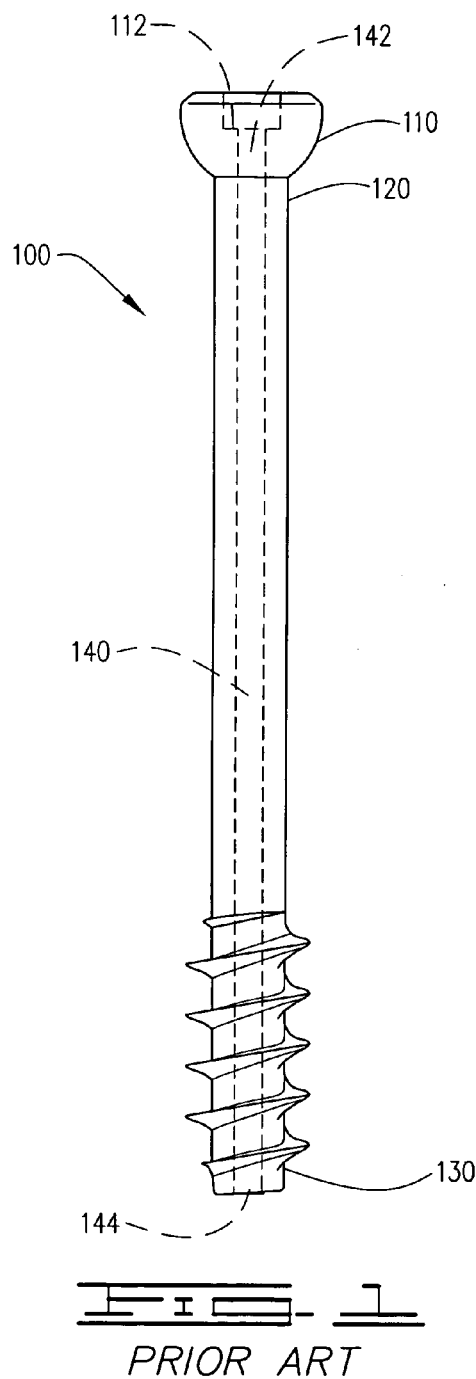
FIG. 1 is a side view of a prior art cannulated surgical screw.
Figure 2A:
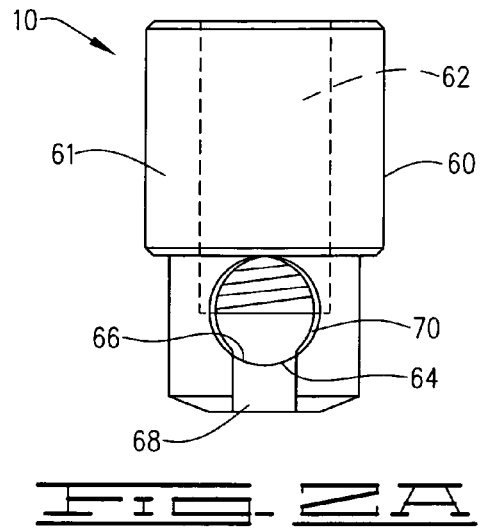
FIG. 2A is a side view of a lower member of the cannulated screw bone filler adapter.
Figure 2B:
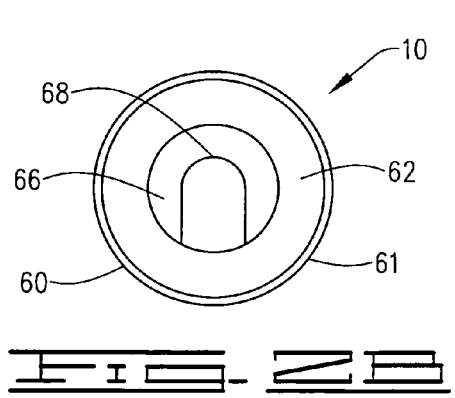
FIG. 2B is a top view of the lower member of the cannulated screw bone filler adapter.
Figure 2C:
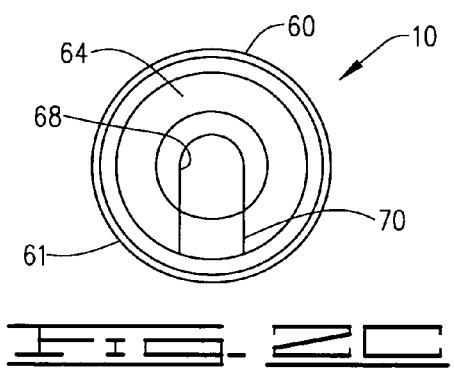
FIG. 2C is a bottom view of the lower member of the cannulated screw bone filler adapter.
Figure 3:
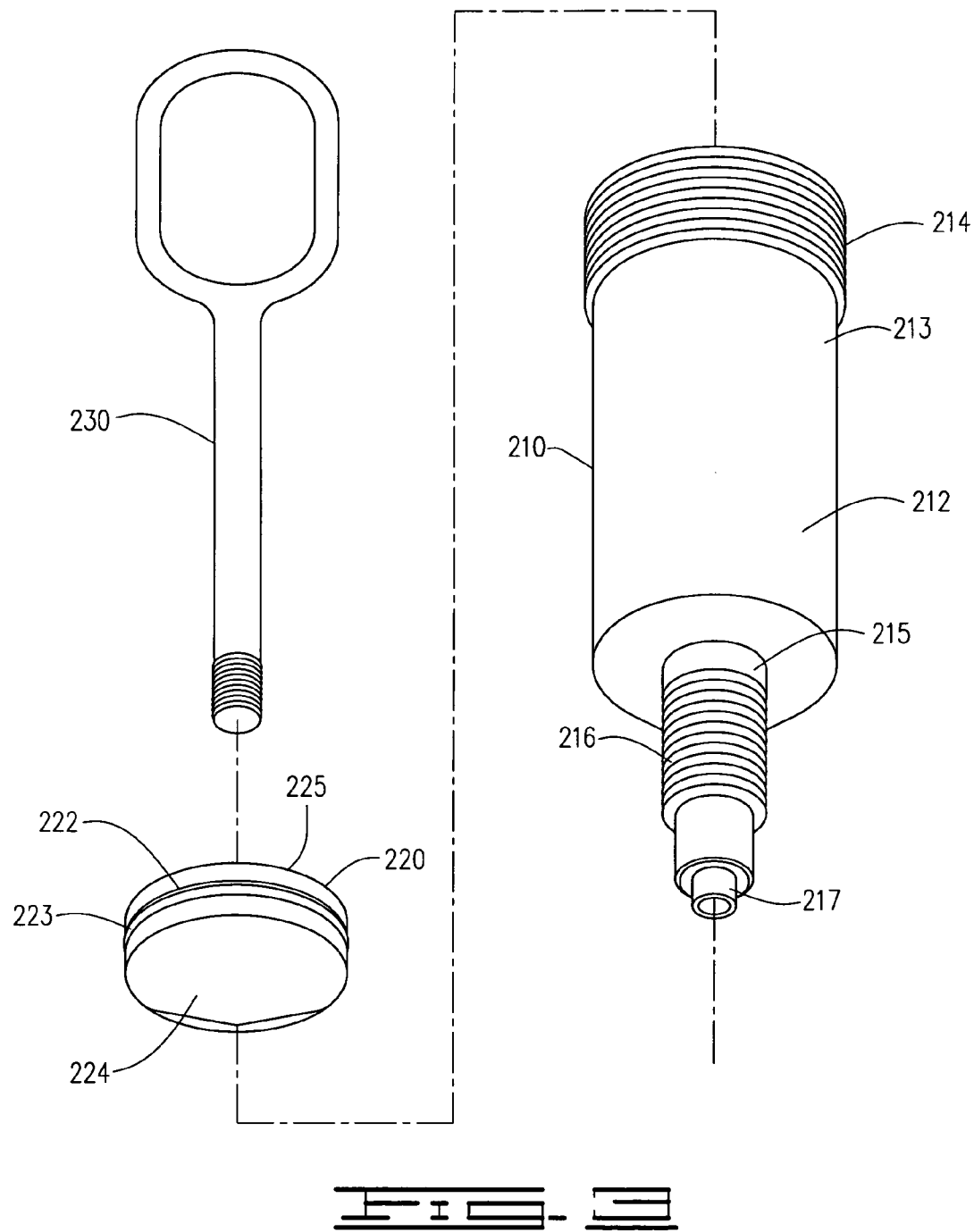
FIG. 3 is an expanded view of the upper syringe body of the cannulated screw bone filler adapter, the inner plunger and the plunger removal tool.

A pressurized syringe assembly 200 to dispense a high viscous liquid, preferably a bone filler cement, attached to an adapter 10 providing a secure connection between a head 110 of an externally threaded cannulated surgical screw 100, indicated in FIGS. 1, 4B, 5B and 6B, defining the head 110, neck 120 and tip 130, to inject a bone filler cement through an upper end 142 of a longitudinal bore 140 in the cannulated surgical screw 100 through a lower end 144 of the longitudinal bore 140 into a bone void z within a bone x undergoing a surgical repair at a fracture site y, FIGS. 7A-B, the pressurized syringe assembly 200, FIGS. 3-6B, providing a syringe body 210 defining an inner cavity 211, an upper body portion 212 having an upper end 213 defining a plurality of upper external threads 214 and a lower narrowed body portion 215 including external threads 216 and defining a terminal cannulated screw insertion nipple 217 upon which is inserted an O-ring seal member 218, a thickened plunger member 220 defining at least one outer channel 222 within which is placed at least one plunger O-ring 223 forming a seal between the thickened plunger 220 against the inner cavity 211 and the syringe body 210, the thickened plunger member 220 forcibly longitudinally directed within the inner cavity 211 of the syringe body 210, a lowered tapered end 224 and an upper end 225 defining a central aperture 226, a grip handle member 240 defining a circular ring 242 having lower internal threads 244 which sealably engage the external threads 214 of the upper end 213 of the syringe body 210, an upper cap portion 246 providing a central threaded bore 248 and an extending handle member 249, a retractable screw member 250 providing an elongated shaft 252 having a plurality of externally threads 254 which engage the central threaded bore 248 of the upper cap portion 246, the crew member 250 further providing an upper end 255 and a lowered end 256 defining a smooth narrowed plunger insertion tip 258 rotatably engaging the central aperture 226 of the plunger 220 when the elongated shaft 252 is inserted through the central threaded bore 248 of the upper cap portion 246 into the inner cavity 211 of the syringe body 210 once the syringe body 210 is filled with the viscous liquid of bone cement, the plunger 220 is inserted within the inner cavity 211, and the grip handle portion 240 is affixed to the syringe body 210, and a spindle 260 having a central threaded screw member bore 262 within which the upper end 255 of the elongated shaft 252 is held, the spindle 260 being turned around an axis 265 defined by the elongated shaft 252, turning the elongated shaft 252 with a force to urge the narrowed plunger insertion tip 258 against the thickened plunger 220, forcing the thickened plunger 220 down through the inner cavity 211 of the syringe body 210, and further forcing the viscous liquid or bone cement below the lower tapered end 224, through the lower narrowed body portion 215 of the syringe body 210 and out of the terminal cannulated screw insertion nipple 217. It is important that the relationship between the narrowed plunger insertion tip 258 and the central aperture 226 of the thickened plunger 220 be freely rotatable to deter potential rotation of the thickened plunger 220 when force through the inner cavity 211 of the syringe body 210 so that the viscous liquid or bone cement within the inner cavity 211 is evenly and smoothly moved down the inner cavity 211 during its injection. The central aperture may be internally threaded, not shown, to receive a threaded plunger retrieval tool 230, shown in FIG. 3, engaging the central aperture 226 after the syringe body 210 is removed from the grip handle portion 240, to remove the thickened plunger 220 from the inner cavity 211 of the syringe body 210 after expulsion of the viscous liquid or bone cement from the syringe body 210 for cleaning and reuse.

The syringe body 210 is further attached to a cannulated surgical screw bone filler adapter 10, the adapter 10 further providing a lower member 60, FIGS. 2A-C, 4B, 5B and 6B, the lower member 60 defining an expanded upper portion 61 providing an internal threaded inner cavity 62 receiving the external threads 216 of the lower narrowed body portion 215 of the syringe body 210, a bottom portion 64 defining a contoured head cradle 66, and a lower circular screw neck support 68 to receive and retain the head and neck of the cannulated screw through the lower cannulated screw adapter insertion port 70, with the terminal cannulated screw insertion nipple 217 of the syringe body 210 being directed and secured within the upper end 142 of the longitudinal bore 140 and within a tool depression 112 within the head 110 of the cannulated screw 100 to prevent spillage or leakage of the viscous liquid or bone filler cement during injection under pressure from the pressurized syringe assembly 200, through the adapter 10 and into the longitudinal bore 140 of the cannulated surgical screw 100.

Figure 6A:
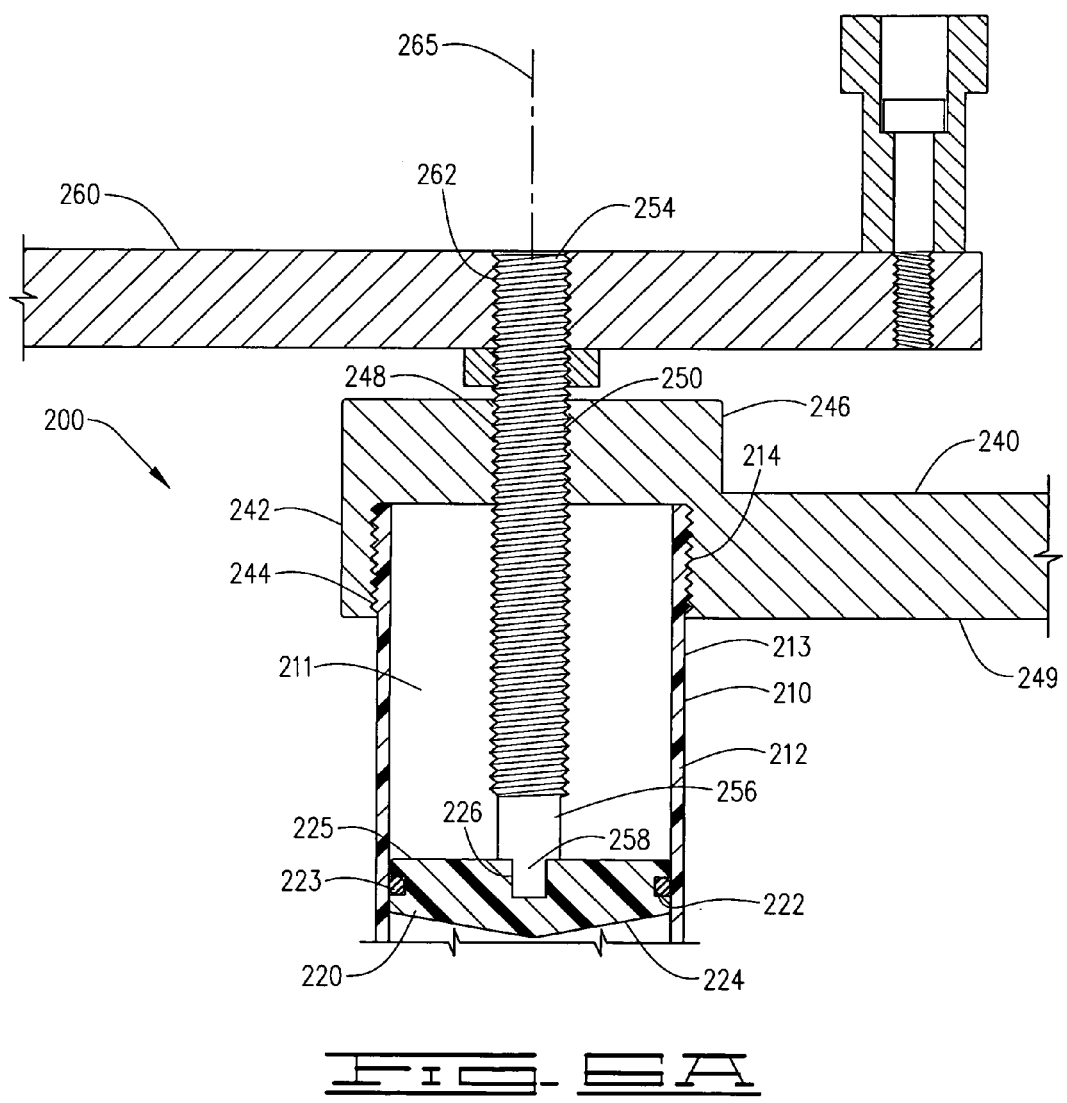
FIG. 6A is a side cross sectional view of the pressurized syringe assembly attached to the cannulated screw bone filler adapter with the plunger in a fully extended position subsequent to the dispensing of a bone filler cement.
Figure 8B:
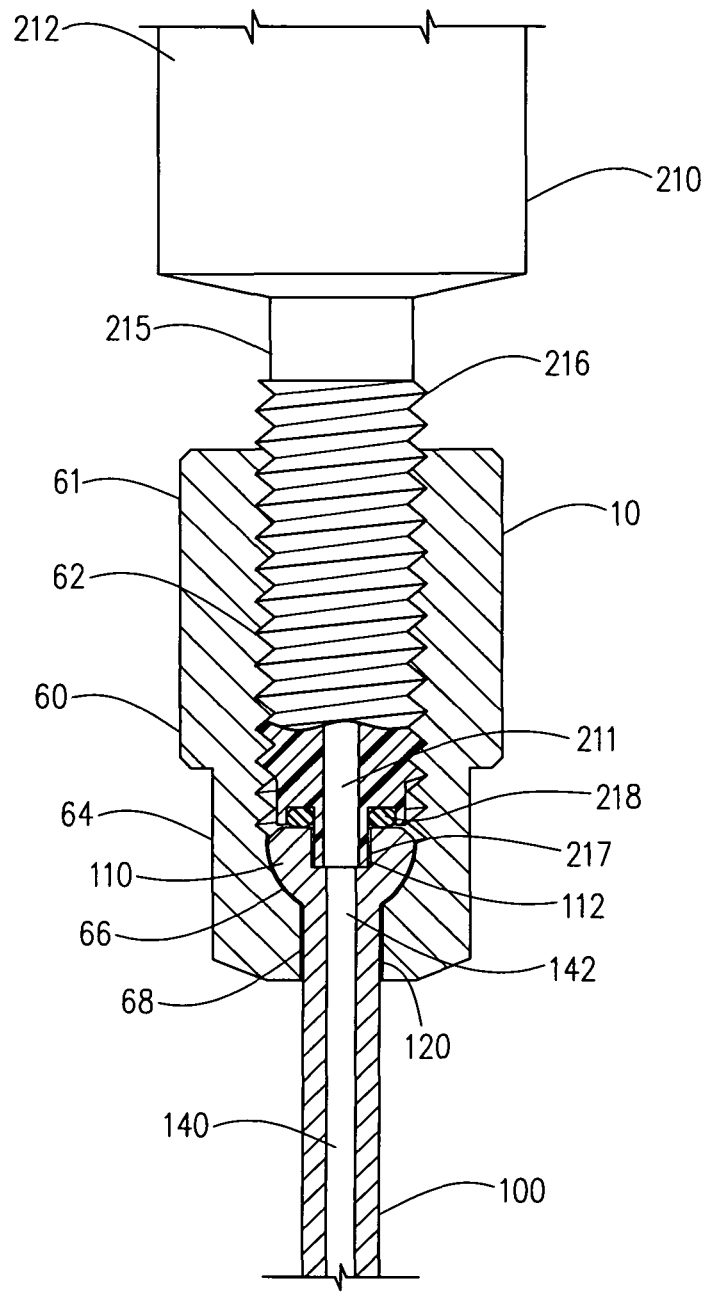

The assembly and relationship of the pressurized syringe assembly 200, through the adapter 10, and into and through the cannulated surgical screw 100 is demonstrated in FIG. 6B, with the terminal cannulated screw insertion nipple 217 completely within the tool depression 112 of the cannulated screw 100 and into the upper end 142 of the longitudinal bore 140, the lower narrowed body portion 215 of the syringe body 210 threadably engaged within the upper expanded portion 61 of the lower member 60, the lower member 60 retaining the head 110 of the inserted cannulated surgical screw 100 thus providing a closed channel between the inner cavity 211 of the syringe body 210 and the longitudinal bore 140 of the cannulated surgical screw 100 all the way through to the lower end 144 of the longitudinal bore 140 at the tip 130 of the cannulated surgical screw 100.

Figure 5A:
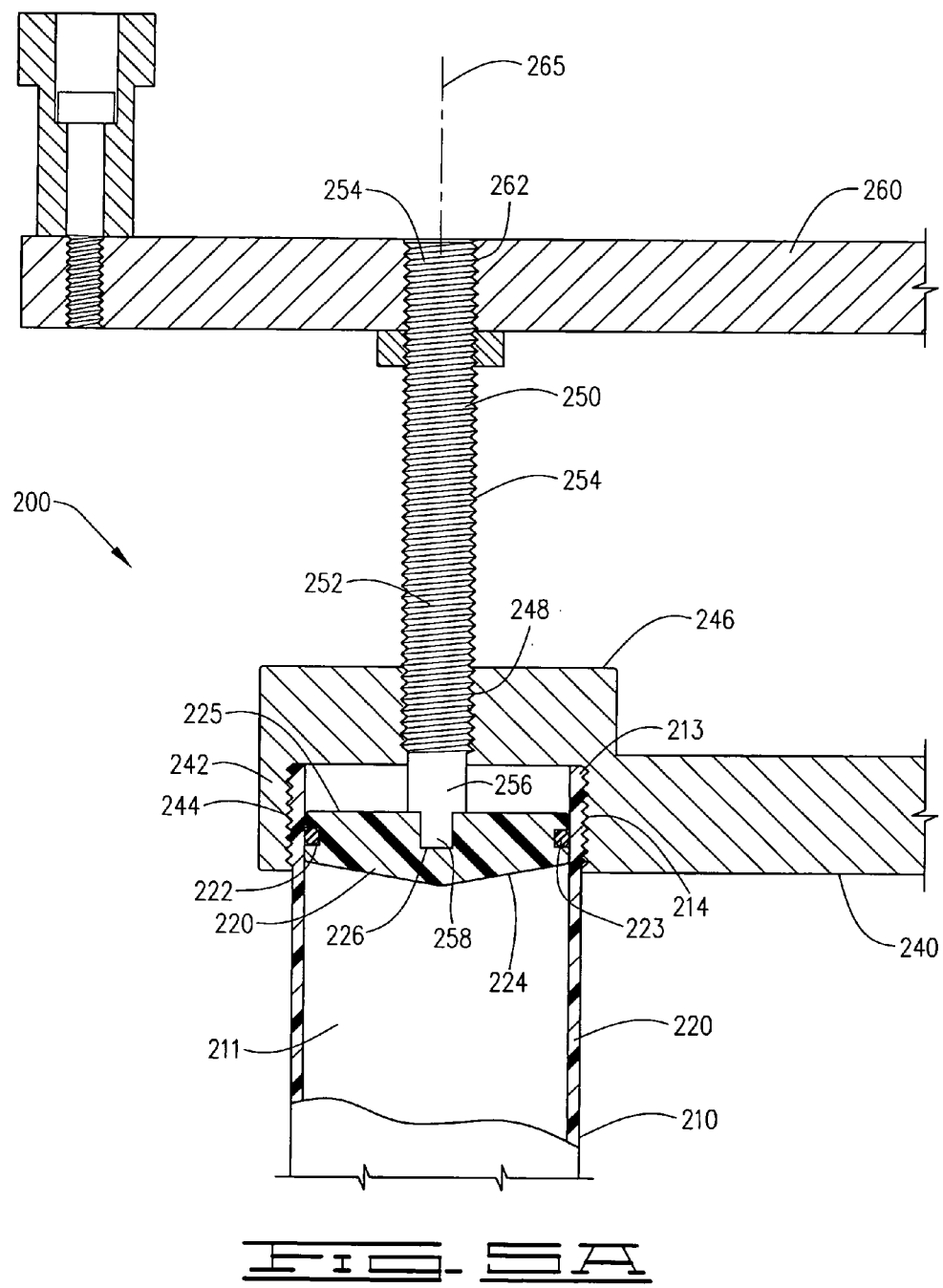
FIG. 5A is a side cross sectional view of the pressurized syringe assembly attached to the cannulated screw bone filler adapter with the plunger in a fully retracted position prior to the dispensing of a bone filler cement.
Figure 5B:
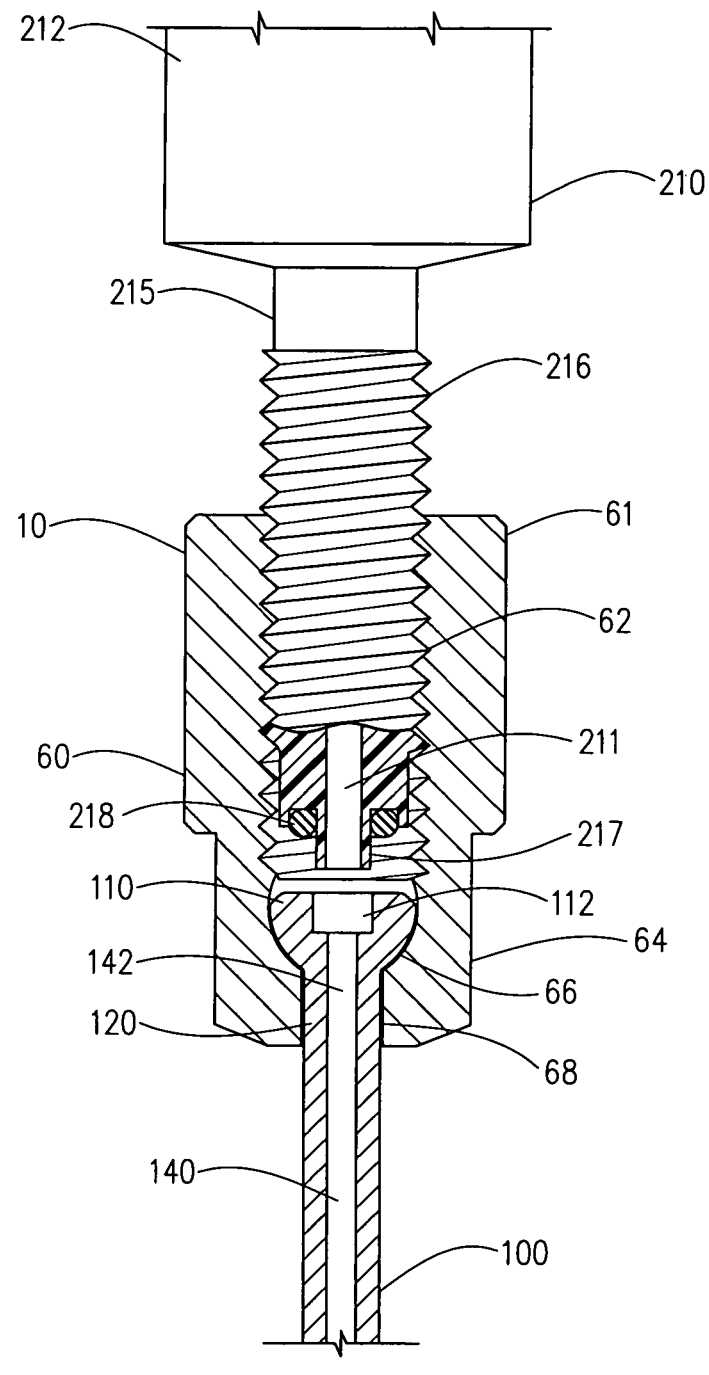
FIG. 5B is a side cross sectional view of the pressurized syringe assembly attached to the cannulated screw bone filler adapter and a cannulated surgical screw with the upper syringe body and the lower member engaged but not secured, positioning the cylindrical tip of the upper member above the upper portion of the longitudinal bore of the cannulated surgical screw, prior to injection of the bone filler through the longitudinal bore and eventually out of the lower end of the longitudinal bore.

Use and application of the pressurized syringe assembly 200 and the cannulated surgical screw bone filler adapter 10 during a surgical procedure to repair a fracture site y of a bone x would occur after a subject bone x is drilled, reduced and subsequent to a full insertion of the cannulated surgical screw 100 penetrating into a bone void z to secure and fix the fractured site y of a bone, as indicated in FIG. 7A. The cannulated surgical screw 100 is then partially rotated back out, as indicated in FIG. 7B. The lower member 60 is then placed over the head 110 of the cannulated surgical screw 100 by sliding the head 110 of the cannulated surgical screw 100 through the lateral cannulated screw adapter insertion port 70, seating the head 110 of the cannulated surgical screw 100 within the contoured head cradle 66 of the lower member 60 with the neck 120 of the cannulated surgical screw 100 extending through the circular screw neck support 68. The lower narrowed body portion 215 of the syringe body 210 is then threadably inserted into the lower member 60 until the screw insertion nipple 217 is completely inserted within the upper end 142 of the longitudinal bore 140 of the cannulated surgical screw 100, FIG. 6B, and within the upper end 52 of the longitudinal bore 50 in the head 110 of the cannulated surgical screw 100, with the O-ring 218 being compressed against the head 110 of the cannulated screw 100 around the tool depression 112 to prevent any leakage of bone filler cement during injection of the bone filler cement. FIG. 5B shows the partial assembly of the adapter 10 and the syringe body 200, with the screw insertion nipple 217 above the tool depression 112 immediately prior to complete insertion and prior to the compression of the O-ring 218 to form a secure seal.

Once secured, the bone filler cement or viscous liquid may be deported from the syringe body 210 using the complete syringe assembly 200, through the longitudinal bore 140 and into the bone void within the subject bone x to fill the bone void with bone filler cement. The pressurized syringe assembly would then be detached from the lower member 60, and the head 110 of the cannulated surgical screw 100 released from the lower member 60 by sliding the lower member 60 away from the head 110 of the cannulated surgical screw 100. After ensuring that no residual bone filler cement is present on the head 110 of the cannulated surgical screw 100, the cannulated surgical screw 100 would then be reinserted fully into the bone x, with the tip 130 of the cannulated surgical screw 100 being set within the bone filler cement which would set to a hard matrix within the bone void z. The method disclosed utilizing the adapter would be identical to the method patent previously filed by the same inventors as reference herein.

The disclosed cannulated surgical screw bone filler adapter 10 used in conjunction with the pressurized syringe assembly 200 provides a secure connection between a cannulated surgical screw 100 and the syringe assembly which has been filled with a quantity of viscous liquid or bone cement to deliver the bone filler cement into a bone void without contaminating the surgical site with leaking liquid or cement, for a secure attachment of the tip 130 of a fully inserted surgical screw 100 into a bone. The disclosed adapter 10 is installed upon the head of the cannulated surgical screw without requiring any hands to hold the adapter 10 on the screw head 110 during application of the syringe assembly 200, allowing one or more hands to be utilized on deporting the viscous fluid or bone cement from the pressurized syringe assembly 200.

The disclosed pressurized syringe assembly 200 may be modified or adapted for use with other existing and available surgical appliances for the evacuation of a viscous fluid without using the adapter 10, or when used with the adapter 10 during other existing or currently used surgical procedure to inject bone filler cement into a directed bone without contamination of the surgical tissue with the bone filler cement. While the invention has been particularly shown and described with reference to a preferred embodiment thereof, it will be understood by those skilled in the art that changes in form and detail may be made therein without departing from the spirit and scope of the invention.

What is claimed is:

1. A pressurized syringe assembly to dispense a bone filler cement directly into a head of an externally threaded cannulated surgical screw defining head, neck and tip, to inject said bone filler cement through an upper end of a longitudinal bore in said cannulated surgical screw through a lower end of said longitudinal bore into a bone void within a bone undergoing a surgical repair at a fracture site comprising:

said pressurized syringe assembly providing a syringe body defining an upper body portion with an upper end having a plurality of external threads and a lower narrowed body portion having a plurality of external threads and a terminal cannulated screw insertion nipple, said syringe body further defining an inner cavity from said upper end to said terminal cannulated screw insertion nipple, a thickened plunger defining a lower tapered end and an upper end having a central aperture, said plunger inserted within said inner cavity within said upper body of said syringe body, a grip handle portion defining a circular ring having lower internal threads receiving said external thread of said upper end of said upper body of said syringe body forming a secure connection, said grip handle portion further defining an upper cap portion having a central threaded bore and an extended handle member, a retractable screw member defining a shaft with external threads, an upper end and a lower end which is inserted through and threadably engaged with the central threaded bore of said upper cap portion of said grip handle portion, said lower end defining a smooth plunger insertion tip which is rotatably inserted within said central aperture of said plunger and a spindle having a central threaded bore securely attaching to said upper end of said screw member to forcibly rotate said screw member to lower said insertion tip forcing said plunger down said inner cavity of said upper body portion of said syringe body to expel said bone cement placed within said inner cavity below said plunger out said insertion nipple of said syringe body; and an adapter further comprising a lower member defining an upper portion with an inner threaded cavity, said inner threaded cavity receiving said outer threads of said lower narrowed body portion of said syringe body forming a secure connection, said adapter further providing a bottom portion defining an inner head cradle to receive said head of said cannulated surgical screw, a lower neck support securing said neck of said cannulated screw, and a side insertion port to insert said head of said cannulated screw within said head cradle, wherein said head of said cannulated screw is placed within said head cradle and said lower narrowed body portion is threaded within said upper portion within said threaded inner cavity directing and securing said insertion nipple within a tool depression directly into said upper end of said longitudinal bore, said adapter directing said insertion nipple within a tool depression directly into said upper end of said longitudinal bore to dispense said bone filler cement from said syringe body directly into said longitudinal bore without and bone filler cement leaking from said syringe body, said adapter or said cannulated screw and expelled only from said lower end of said terminal cannulated screw insertion nipple of said cannulated screw into the bone void within which said cannulated surgical screw has been installed.

2. The pressurized syringe assembly, as disclosed in claim 1, further comprising:

said insertion nipple further defining a compressible O-ring surrounding said insertion nipple, said cylindrical tip being compressible forming a seal against said head of said cannulated surgical screw when said lower narrowed body portion is fully inserted within said threaded inner cavity of said lower member to further prevent spillage or leakage of the bone filler cement during injection under pressure from said syringe body, through said central bore in said upper member, and into a lower end of said longitudinal bore of said cannulated surgical screw; and said plunger further defining at least one outer channel within which is located at least on compressible O-ring forming a seal against said inner cavity of said upper body portion of said syringe body to prevent said bone filler cement from leaking around said plunger during injection of said bone filler cement from said pressurized syringe assembly.

* * * * *